(12) United States Patent
Yokoo

(10) Patent No.: US 11,078,455 B2
(45) Date of Patent: Aug. 3, 2021

(54) CLOSED CULTURE VESSEL FOR ADHERENT CELLS

(71) Applicant: Seiichi Yokoo, Kyoto (JP)

(72) Inventor: Seiichi Yokoo, Kyoto (JP)

( * ) Notice: Subject to any disclaimer, the term of this patent is extended or adjusted under 35 U.S.C. 154(b) by 42 days.

(21) Appl. No.: 15/311,880

(22) PCT Filed: Jun. 9, 2015

(86) PCT No.: PCT/JP2015/002888
§ 371 (c)(1),
(2) Date: Nov. 17, 2016

(87) PCT Pub. No.: WO2015/190090
PCT Pub. Date: Dec. 17, 2015

(65) Prior Publication Data
US 2017/0114315 A1    Apr. 27, 2017

(30) Foreign Application Priority Data
Jun. 9, 2014    (JP) .............................. JP2014-118973

(51) Int. Cl.
*C12M 1/12*    (2006.01)
*C12M 3/00*    (2006.01)
(Continued)

(52) U.S. Cl.
CPC ............ *C12M 37/02* (2013.01); *C12M 23/14* (2013.01); *C12M 23/24* (2013.01); *C12M 23/48* (2013.01);
(Continued)

(58) Field of Classification Search
CPC ...... C12M 37/02; C12M 23/14; C12M 23/24; C12M 23/48; C12M 29/20; C12M 33/00; C12M 37/04
See application file for complete search history.

(56) References Cited

U.S. PATENT DOCUMENTS 4,829,002 A * 5/1989 Pattillo .................. C12M 23/14
435/297.1
4,847,462 A * 7/1989 Soodak ............... B29C 65/7847
219/121.63
(Continued)

FOREIGN PATENT DOCUMENTS

JP    2004141143 A    5/2004
JP    2005-514056 A    5/2005
(Continued)

OTHER PUBLICATIONS

Extended European Search Report issued in European application No. EP 15807032.6 dated Dec. 20, 2017.
(Continued)

*Primary Examiner* — William H. Beisner
*Assistant Examiner* — Danielle B Henkel
(74) *Attorney, Agent, or Firm* — Pearne & Gordon LLP

(57) ABSTRACT

The present invention provides a culture vessel with which cells can be aseptically cultured and aseptically transferred to a place where the cells are to be used (such as an operating room) and from which the cells can be simply taken out. The present invention provides a closed culture vessel including an openable airtight vessel, and a cell culture member disposed in the airtight vessel and including a cell culture surface, in which the cell culture member is provided detachably from the airtight vessel.

7 Claims, 23 Drawing Sheets

(51) Int. Cl.
*C12M 1/00* (2006.01)
*C12M 1/04* (2006.01)
*C12M 1/26* (2006.01)

(52) U.S. Cl.
CPC ............ *C12M 29/20* (2013.01); *C12M 33/00* (2013.01); *C12M 37/04* (2013.01)

(56) References Cited

U.S. PATENT DOCUMENTS

| | | | |
|---|---|---|---|
| 5,602,028 | A | 2/1997 | Minchinton |
| 6,461,853 | B1 | 10/2002 | Zhu |
| 7,718,423 | B2 * | 5/2010 | Tsuchiya ............ G01N 21/0332 219/201 |
| 2004/0005699 | A1 * | 1/2004 | Roos .................... C12M 23/24 435/297.5 |
| 2005/0084954 | A1 | 4/2005 | Bader |
| 2005/0107876 | A1 * | 5/2005 | Kim ........................ A61L 27/58 623/15.12 |
| 2005/0248836 | A1 * | 11/2005 | Tsuchiya ............ G01N 21/0332 359/368 |
| 2008/0009027 | A1 * | 1/2008 | Fraker .................... C12M 23/04 435/29 |
| 2009/0017092 | A1 * | 1/2009 | Dutta .................. C12N 5/0068 424/423 |
| 2010/0062530 | A1 * | 3/2010 | Tanaka ................... C12M 27/02 435/383 |
| 2011/0129923 | A1 * | 6/2011 | Wilson .................. C12M 25/06 435/395 |
| 2012/0094372 | A1 * | 4/2012 | Mukhopadhyay ..... C12M 23/20 435/297.1 |
| 2014/0205646 | A1 * | 7/2014 | Morse ................ A61L 27/3687 424/423 |
| 2015/0231628 | A1 | 8/2015 | Nozaki et al. |
| 2015/0252314 | A1 * | 9/2015 | Onji ........................ C12Q 1/04 435/39 |
| 2016/0177245 | A1 * | 6/2016 | Johnson ................. C12M 23/14 435/401 |
| 2016/0177250 | A1 * | 6/2016 | Arm ....................... C12M 37/04 435/29 |
| 2016/0208207 | A1 * | 7/2016 | Sugiura ................. C12M 23/58 |

FOREIGN PATENT DOCUMENTS

| | | | |
|---|---|---|---|
| JP | 2005-531327 A | 10/2005 | |
| JP | 2006-320226 A | 11/2006 | |
| JP | 2008-271850 A | 11/2008 | |
| JP | 2009542230 A | 12/2009 | |
| JP | 2011-160729 A | 8/2011 | |
| JP | 2013-128458 A | 7/2013 | |
| WO | 2008131973 A2 | 11/2008 | |
| WO | 2009088023 A1 | 7/2009 | |
| WO | 2010049181 A1 | 5/2010 | |
| WO | WO-2013166525 A2 * | 11/2013 | ............ C12M 45/22 |
| WO | 2013183121 A1 | 12/2013 | |
| WO | 2014041593 A1 | 3/2014 | |
| WO | 2014054494 A1 | 4/2014 | |
| WO | 2015076115 A1 | 5/2015 | |
| WO | 2015111348 A1 | 7/2015 | |

OTHER PUBLICATIONS

Utheim, Tor Paaske, et al. "A novel method for preserving cultured limbal epithelial cells." British Journal of Ophthalmology 91.6 (2007): 797-800.

International Search Report dated Sep. 29, 2015 for PCT/JP2015/002888.

Uthiem, TP, et al. "Sterility control and long-term eye-bank storage of cultured human limbal epithelial cells for transplantation." Br. J. Ophthalmol., 2009, vol. 93, No. 7, p. 980-983.

Office Action for Japanese Patent Application No. 2016-527638 dated Jan. 7, 2020, pp. 1-3 (see p. 3 for list of references cited).

* cited by examiner

CLOSED CULTURE VESSEL FOR ADHERENT CELLS

TECHNICAL FIELD

The present invention relates to a culture vessel with which cells can be aseptically cultured and aseptically transferred to a place where the cells are to be used (such as an operating room or a cultivation room) and from which the cells can be simply taken out.

BACKGROUND ART

In recent years, regenerative medicine has been remarkably developed, and various techniques for culturing cells under feeder-free and xeno-free conditions or techniques for aseptically culturing cells have been developed.

A cell processing facility (CPF), that is, facilities where the cleanliness of whole laboratories is highly kept for performing a culture operation, has been installed and an environment where contamination risk is reduced has been realized, but construction, maintenance, and running cost of the facilities are very expensive. Therefore, in order to reduce such costs, an isolator and the like with which a culture operation can be performed under a closed culture environment has also been developed. The maintenance of an isolator is, although less expensive than that of CPF, still as expensive as several tens of millions of yen per each. A system developed to cope with merely a specific cell type for price reduction is still expensive.

Besides, according to the recent development of the regenerative medicine, regenerative medical techniques using autologous cells have been actively developed. It is necessary to prepare cells separately for every person, and it is also a serious problem that the facilities such as the CPF or the isolator are occupied by the culture of cells of one person.

Furthermore, although expensive investment is thus required for facilities and equipment for culture, change of such facilities and equipment directly results in change of production procedures, and this change affects production protocol for a regenerative medical product produced as an investigational new drug, a pharmaceutical drug or pharmaceutical equipment, which causes a serious problem requiring significant costs and efforts in, for example, gaining manufacturing approval again.

Here, for example, Patent Literature 1 discloses a closed culture vessel for preventing degradation of a culture medium. This culture vessel is a vessel for culturing suspended cells, and the disclosed vessel can be increased in the culture volume in accordance with culture time. The vessel disclosed in Patent Literature 1 is, however, a vessel for culturing suspended cells, and is not intended to be used for culturing adherent cells.

Alternatively, as a technique for enabling adherent cells to be aseptically cultured, to be aseptically transferred to a place where the cells are to be used (such as an operating room), and to be simply taken out, Patent Literature 2 discloses a transportation vessel that can be aerially transported. But it is necessary to tightly seal, in a CPF or the like, tissue for transplantation having been cultured in a CPF or the like in such a vessel, which requires expensive aseptic facilities and equipment.

CITATION LIST

Patent Literature

Patent Literature 1: Japanese Patent Laid-Open No. 2008-271850
Patent Literature 2: Japanese Patent Laid-Open No. 2013-128458

SUMMARY OF INVENTION

The present invention provides a very inexpensive culture vessel applicable to various cells, with which cells can be aseptically cultured and aseptically transferred to a place where the cells are to be used (such as an operating room) and from which the cells can be simply taken out, without requiring expensive aseptic facilities and equipment, and hence without largely changing production protocol accompanying change of facilities or equipment or with a new approval application avoided.

Specifically, the present invention provides the following:

(1) A closed culture vessel for adherent cells, including: an openable airtight vessel; and a cell culture member disposed in the airtight vessel and having a cell culture surface, in which the cell culture member is provided detachably from the airtight vessel.

(2) The culture vessel according to (1) above, in which the cell culture member includes: a bottom surface having the cell culture surface; and a side surface extending upward from a circumferential edge of the bottom surface.

(3) The culture vessel according to (2) above, in which the side surface extending upward from the circumferential edge of the bottom surface of the cell culture member is non-cell-adhesive.

(4) The culture vessel according to (1) above, in which the cell culture member is a substrate having the cell culture surface.

(5) The culture vessel according to any one of (1) to (4) above, in which the airtight vessel is a vessel including gas exchange means capable of aseptic gas exchange for aseptically performing gas exchange between inside and outside of the airtight vessel.

(6) The vessel according to any one of (1) to (5) above, in which the gas exchange means capable of aseptic gas exchange is a filter capable of performing gas exchange between inside and outside of the airtight vessel.

(7) The vessel according to any one of (1) to (6) above, in which the airtight vessel is a gas permeable cell culture bag.

(8) The culture vessel according to any one of (1) to (7) above, in which only the cell culture surface of the cell culture member is cell-adhesive and/or another surface of the member and an inner surface of the airtight vessel are non-cell-adhesive.

(9) The culture vessel according to any one of (1) to (8) above, in which the airtight vessel includes a cell inlet through which a member having adherent cells adhered to a cell adhesion surface is capable of being aseptically introduced, and the cell inlet is sealable after introducing the cells.

(10) The culture vessel according to any one of (1) to (9) above, in which the airtight vessel includes a holding projection for externally holding the cell culture member.

(11) The culture vessel according to any one of (1) to (10) above, in which the member has a grip on an edge or a side wall of the substrate.

(12) The culture vessel according to any one of (1) to (11) above, in which the cell culture member includes: a bottom surface having the cell culture surface; and a side surface extending upward from a circumferential edge of the bottom surface, and the side surface is detachable from the cell culture surface of the member.

(13) The culture vessel according to any one of (1) to (12) above, further including a saucer for receiving a culture medium having been placed in the airtight vessel.

(14) A set including a sealable and openable airtight vessel and a cell culture member having a cell culture surface.

(15) The set according to (14) above, in which the airtight vessel includes a holding projection for externally holding the cell culture member.

(16) The set according to (14) or (15) above, further including a saucer for receiving a culture medium having been placed in the airtight vessel.

(17) A closed cell culture system, including: the culture vessel according to any one of (1) to (13) above; a medium supply means for supplying a culture medium to the culture vessel; and a medium discharge means for discharging the culture medium from the culture vessel.

According to the present invention, it is possible, at the time of culture, to perform the culture under an aseptic closed environment, and it is possible, after completing the culture, to aseptically transfer cultured cells to a place where the cells are to be used. Besides, according to the present invention, a cell culture member can be easily taken out of the vessel as well as the culture member thus taken out can be immediately used. In other words, according to the present invention, the aseptic closed environment can be retained not only during the culture but also during the transfer of the culture member without requiring expensive aseptic facilities or equipment, and the culture member can be taken out of the vessel in a medical setting to be used there, and therefore, the present invention is extremely advantageous in that a possibility of contamination of the culture member can be made just about nil by a simple and inexpensive method. Furthermore, according to the present invention, various open cell culture vessels or substrates can be used as the cell culture member. In other words, a variety of closed culture vessels can be simply and inexpensively produced by the present invention.

DESCRIPTION OF EMBODIMENTS

Herein, a cell is not specifically limited but is, for example, a corneal epithelial cell, a corneal epithelial stem cell, a corneal endothelial cell, a corneal endothelial stem cell, an oral mucosal epithelial cell, an oral mucosal epithelial stem cell, a conjunctival epithelial cell, a conjunctival epithelial stem cell, a skin epithelial cell or a skin epithelial stem cell.

In the following embodiments, any of all consistent combinations can be employed.

First Embodiment

A first embodiment will now be described with reference to FIGS. 1 to 3.

(Closed Culture Vessel)

Figure 1:
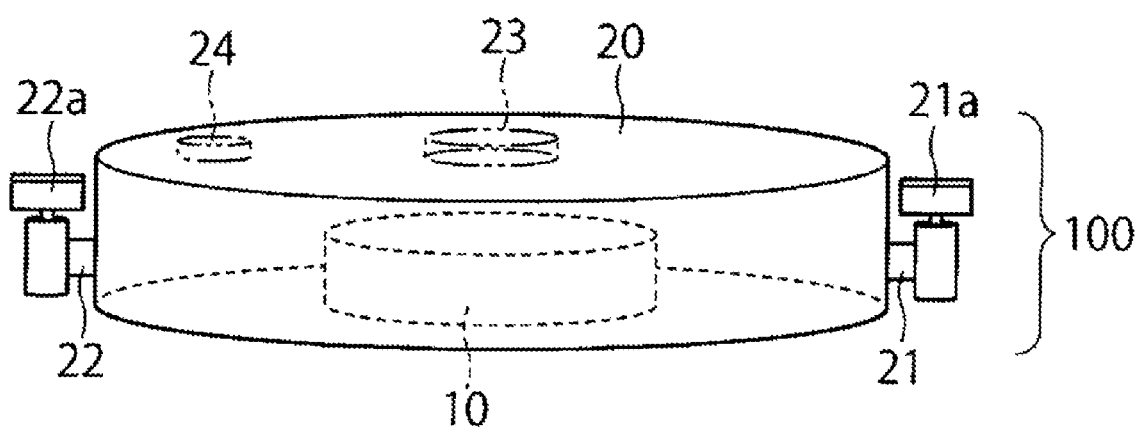
FIG. 1 is a diagram of a closed culture vessel 100 according to a first embodiment.
Figure 2:
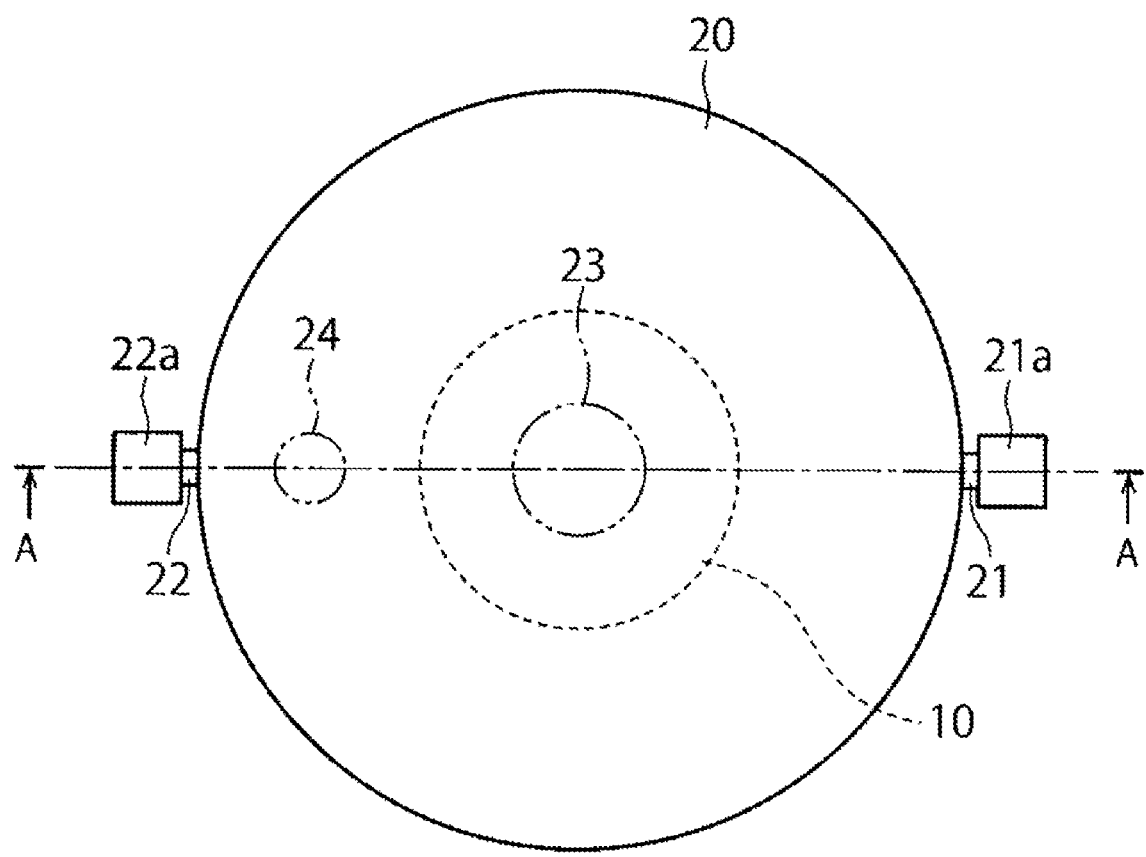
FIG. 2 is a plan view of the closed culture vessel 100 of the first embodiment.
Figure 3:
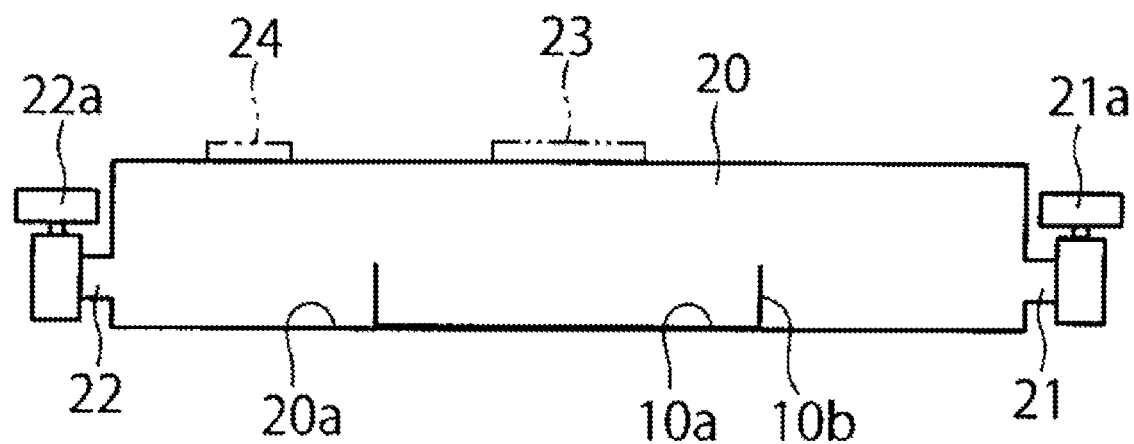
FIG. 3 is a cross-sectional view taken on line A-A of FIG. 2.
Figure 4:
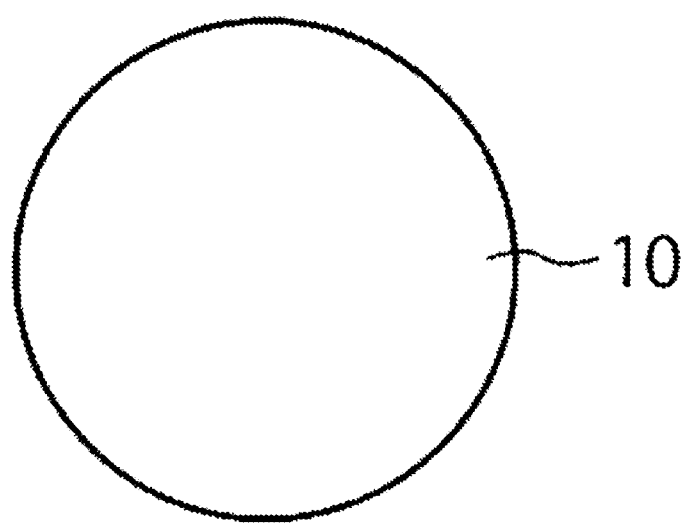
FIG. 4 is a plan view of a cell culture member 10.
Figure 5:
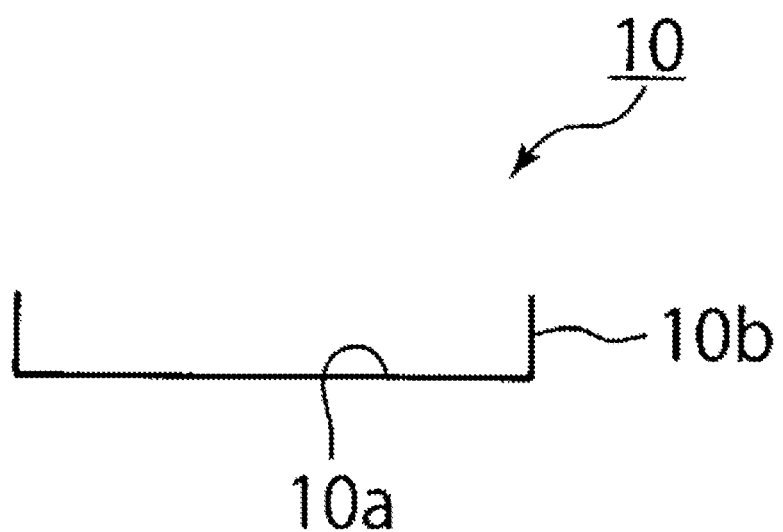
FIG. 5 is a cross-sectional view of the cell culture member 10.

A closed culture vessel 100 of this embodiment includes, as illustrated in FIGS. 1, 2 and 3, an openable airtight vessel 20 and a cell culture member 10 disposed within the airtight vessel and having a cell culture surface. In the airtight vessel 20, the cell culture member 10 configured separately from the airtight vessel 20 is disposed detachably from the airtight vessel.

In the airtight vessel 20, a space having a cultivation room therein, a culture solution inlet 21 through which a culture solution is introduced into the airtight vessel 20, and a culture solution outlet 22 through which the culture solution is discharged from the airtight vessel 20 are provided. The inside of the airtight vessel 20 is kept in an aseptic state, and a culture solution is aseptically introduced through the inlet 21 into the space within the airtight vessel 20. Besides, the culture solution is discharged through the outlet 22 to outside the airtight vessel 20.

In one aspect, the culture solution inlet 21 and the culture solution outlet 22 are respectively provided with an on-off valve 21a and an on-off valve 22a, so that the culture solution inlet 21 and the culture solution outlet 22 can be closed. The on-off valve provided in the culture solution inlet 21 is preferably a valve capable of adjusting an introduction rate of the culture solution. It is not always necessary to provide the valve in the culture vessel 100, but the valve may be provided in a tube connected to the culture solution inlet 21 or the culture solution outlet 22 for supplying or discharging a culture medium. Examples of the valve provided in such a tube include a clamp used for an infusion tube. If the airtight vessel 20 is transferred, the culture solution inlet 21 and the culture solution outlet 22 can be sealed respectively with plugs such as a rubber plug.

Although not restrictive, an inner surface of the airtight vessel 20 is non-cell-adhesive, and is preferably subjected to neither a surface treatment for an adhesive surface nor cell-adhesive coating. The inner surface of the airtight vessel 20 is preferably provided with a non-cell-adhesive coating.

Although not restrictive, the airtight vessel 20 is preferably a vessel capable of aseptic gas exchange between the inside and the outside thereof, and is provided with gas exchange means 24 capable of aseptic gas exchange, such as a vent cap. As a vent cap capable of aseptic gas exchange, a vent cap performing gas exchange through a hydrophobic membrane is commercially available to be used as the gas exchange means 24 of the airtight vessel 20 of the present invention. The hydrophobic membrane may have a pore having a diameter of, for example, 1 μm or less or 0.5 μm or less. Since the gas exchange can be performed between the inside and the outside of the airtight vessel 20, a gas concentration of oxygen, carbon dioxide or the like in the culture medium can be easily kept constant.

Although not restrictive, the airtight vessel 20 is preferably a vessel capable of aseptic gas exchange between the inside and the outside thereof, and in one specific aspect, at least a part of a wall of the vessel is made of a material capable of aseptic gas exchange between the inside and the outside of the vessel, and in a more preferred aspect, the airtight vessel 20 is a gas permeable cell culture bag. A gas permeable cell culture bag is commercially available to be suitably used as the airtight vessel 20. The gas permeable cell culture bag is advantageous in that it can be easily opened, for example, with a knife. Besides, the gas permeable cell culture bag is advantageous in that it can be sealed by sealing with a commercially available sealer after introducing the cell culture member 10 having cells adhered to the cell culture surface. Furthermore, a space can be formed inside the gas permeable cell culture bag by filling it with a culture medium and optionally a gas, and hence, the cell culture surface and the cells adhered thereto can be protected from physical damage. The gas permeable cell culture bag keeps a gas concentration in the culture medium disposed therein at a concentration suitable to the cell culture.

The airtight vessel 20 is an openable airtight vessel. The airtight vessel 20 can be opened after completing culture, and after opening the vessel, the cell culture member 10 can be taken out of the airtight vessel 20.

In order that the vessel can be opened, the airtight vessel 20 may be provided with a lid (not shown) in a shape allowing the cell culture member 10 to be taken out. Besides, the cell culture member 10 can be taken out of the airtight vessel 20 through a cell inlet 23 described below. Alternatively, the airtight vessel 20 may be provided with a region that can be cut with scissors or a knife such as a surgical knife, or the entire airtight vessel 20 may be made of a material that can be cut with a knife, or a part of the airtight vessel 20 may be heat-sealed with a film in a peelable manner, so that the cell culture member 10 can be taken out of the airtight vessel 20.

The airtight vessel 20 can be provided in a state where the cell culture member 10 is precedently disposed inside. In this manner, the inside of the airtight vessel 20 can be easily kept in an aseptic environment.

Besides, the airtight vessel 20 can be a vessel into which the cell culture member 10 having cells adhered to the cell culture surface 10a can be introduced and that can be sealed after the introduction. In this manner, there is no need to seed cells in the entire airtight vessel 20, and thus the amount of cells to be seeded can be reduced.

Besides, the airtight vessel 20 can be provided in the state where the cell culture member 10 has been precedently disposed inside, but can be a vessel from which the cell culture member 10 can be taken out, and in which the cell culture member 10 can be sealed again after seeding cells on the cell adhesion surface 10a. Thus, the cell culture member 10 can be provided in a state where it is aseptically kept in the airtight vessel 20, for example, when sold. The airtight vessel 20 may be further provided with the cell inlet 23 through which cells can be supplied to the inside and that can be sealed. The sealing may be performed using a rubber plug or means such as a seal. If the cell inlet 23 is sealed with a rubber plug, for example, cells can be aseptically introduced into the airtight vessel 20 with a syringe equipped with a needle penetrating through the rubber plug or the like in the cell inlet without unplugging the rubber plug, and after introducing the cells, for example, a hole formed in the rubber plug with the needle can be sealed with a resin or the like, and thus, the aseptic state inside the airtight vessel can be kept. The cell inlet 23 may be in a size sufficiently large for taking or introducing the cell culture member 10 out of or into the airtight vessel therethrough.

The cell culture member 10 includes a bottom surface 10a having the cell culture surface and a side surface 10b extending upward from a circumferential edge of the bottom surface. The bottom surface 10a having the cell culture surface has been subjected to a surface treatment for an adhesive surface so that adherent cells can adhere thereto. Besides, the side surface 10b of the cell culture member 10 is preferably subjected to neither the surface treatment for an adhesive surface nor the cell-adhesive coating. The side surface 10b extending upward from the circumferential edge of the bottom surface of the cell culture member 10 is preferably provided with a non-cell-adhesive coating. The surface treatment for an adhesive surface can be performed by techniques known in this field such as a plasma treatment.

In one aspect of the present invention, the airtight vessel 20 is provided with a plurality of culture solution inlets 21.

In this aspect, the culture solution inlets 21 can be respectively connected to tanks into which a fresh culture solution has been introduced. For example, a first tank is connected to a first inlet 21 so as to introduce the fresh culture medium held in the tank into the airtight vessel 20. Thereafter, when the fresh culture solution held in the tank has been consumed or has lost its freshness, a second tank is connected to a second inlet 21 so as to introduce the fresh culture solution held therein into the airtight vessel 20. In this manner, a culture medium having high freshness can be continuously supplied to the airtight vessel 20. In this aspect, the culture solution inlet 21 connected to the first tank may be closed when the first tank is not needed. The culture solution inlet 21 can be closed with a valve or a clamp. Alternatively, the culture solution inlet 21 may be provided with a portion made of a sealable film material so as to close the portion with a sealer.

In the present invention, the volume of the culture solution can be increased by increasing the capacity of the airtight vessel 20, and thus, composition change of the culture medium can be reduced so as to reduce the replacement frequency. Besides, the increase of the capacity of the airtight vessel 20 has a merit that a stable culture environment can be provided also for cells rapidly degrading the culture medium. In one aspect, the capacity of the airtight vessel 20 is twice or more, three times or more, four times or more, five times or more or ten times or more as large as the capacity of the cell culture member 10.

The planar shape of the cell culture member 10 is not especially limited, and is preferably a circle, an ellipse, a rectangle or a regular polygon such as a square or a regular hexagon.

The cell culture member 10 is placed detachably from the airtight vessel 20. In other words, the cell culture member 10 is constituted separately from the airtight vessel 20. Therefore, the cell culture member 10 and cells adhered to the cell culture surface 10a can be taken out of the airtight vessel 20, and when taken out, a subsequent operation, such as peeling of the cells from the cell culture member 10 or appropriate processing of peripheral portions of the cells, can be easily performed. In one aspect, the cell culture member 10 is simply put in the airtight vessel 20 so that the cell culture member 10 can be easily taken out of the airtight vessel 20.

In one aspect, the cell culture member 10 is removably placed in the airtight vessel 20. In other words, in this aspect, the cell culture member 10 can be introduced into the airtight vessel 20, and can be detached therefrom. For example, after seeding cells in the cell adhesion surface 10a, the cell culture member 10 is aseptically introduced into the airtight vessel 20 and the vessel is sealed, and thereafter, the cells can be cultured. The cell culture member 10 can be taken out of the airtight vessel 20 and introduced into the airtight vessel 20 through the cell inlet 23.

As described above, the cell culture member 10 is detachably placed on the bottom of the airtight vessel 20. Thus, the cell culture member 10 can be taken out of the airtight vessel 20, and cells adhered to the cell culture member 10 can be easily handled. Besides, various cells can be cultured using the same airtight vessel 20 by using cell culture members 10 respectively having cell culture surfaces suitable for the cells to be cultured. Furthermore, a variety of open culture vessels can be introduced as the cell culture member 10 into the airtight vessel 20. For example, in one preferable aspect, the cell culture member 10 is a cell culture dish. Thus, there is no need to prepare a new mold for each closed culture vessel, and hence there is a merit that a variety of culture vessels can be produced at low cost. Specifically, in the present invention, any of various open culture vessels (that can be commercially available products) can be sealed and sterilized in the airtight vessel 20, so that the various open culture vessels can be inexpensively and simply changed into closed culture vessels. Accordingly, the present invention provides a method for producing a closed culture vessel including detachably placing an open culture vessel in an airtight vessel, and then sealing the airtight vessel.

The cell culture member 10 preferably has a grip on the side surface. The cell culture member 10 can be easily taken out of the airtight vessel by gripping the grip. The grip is preferably subjected to neither the surface treatment for an adhesive surface nor the cell-adhesive coating, and is more preferably subjected to the non-cell-adhesive coating.

In one aspect, the bottom surface 10a having the cell culture surface of the cell culture member 10 is made of a membrane. An example of the cell culture member having the bottom surface 10a made of a membrane includes Trans Well (TM) (manufactured by Corning Inc.).

Figure 14:
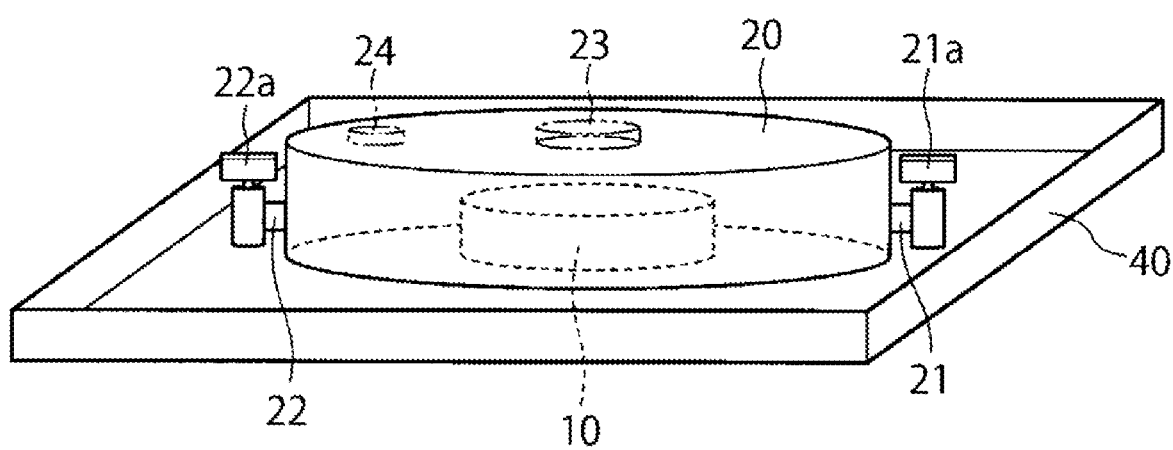
FIG. 14 is a diagram of the closed culture vessel 100 of the first embodiment further provided with a saucer.
Figure 15:
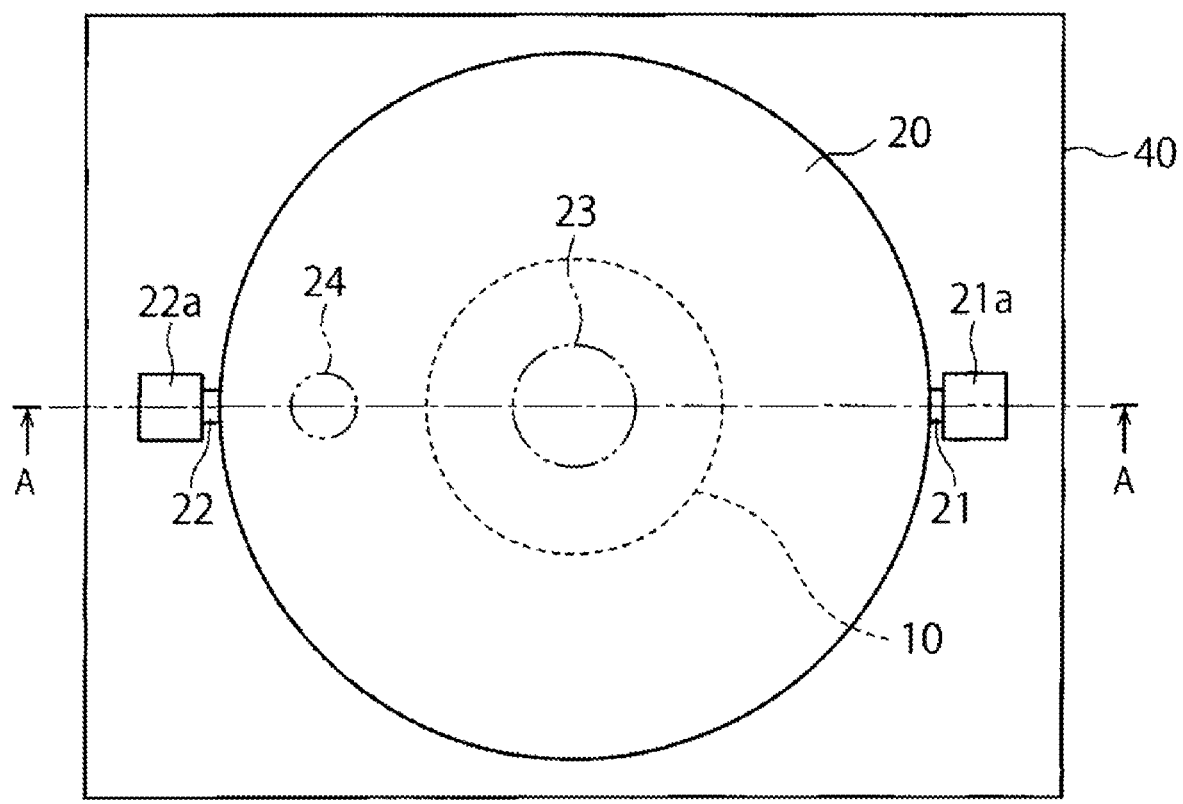
FIG. 15 is a plan view of the closed culture vessel 100 of the first embodiment further provided with the saucer.
Figure 16:
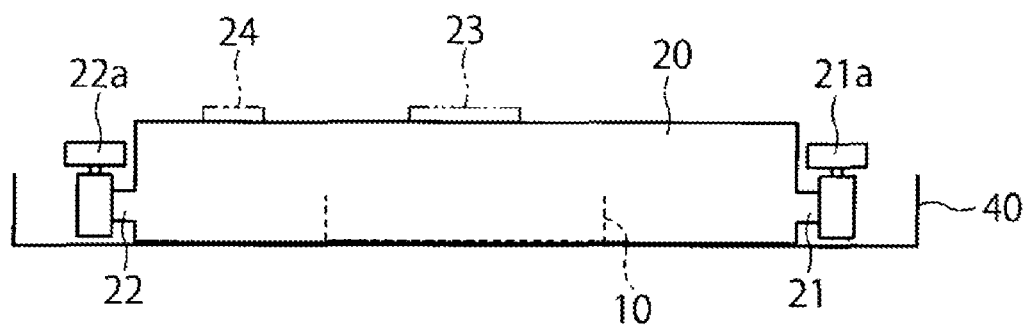
FIG. 16 is a cross-sectional view taken on line A-A of FIG. 12.

The closed culture vessel of the present embodiment may further include a saucer 40 for receiving the medium contained in the airtight vessel 20 as illustrated in FIGS. 14 to 16. Besides, the saucer 40 may be constituted integrally with or separately from the airtight vessel 20. The saucer 40 works as a saucer for the culture medium overflowing from the airtight vessel upon opening the airtight vessel 20, and it is advantageous that the culture medium overflowing from the airtight vessel is prevented from contaminating a surrounding portion. The saucer 40 can be also advantageously used so that closed culture vessels can be aligned in an incubator utilizing the shape of the edge of the saucer 40.

(Closed Culture System)

Figure 17:
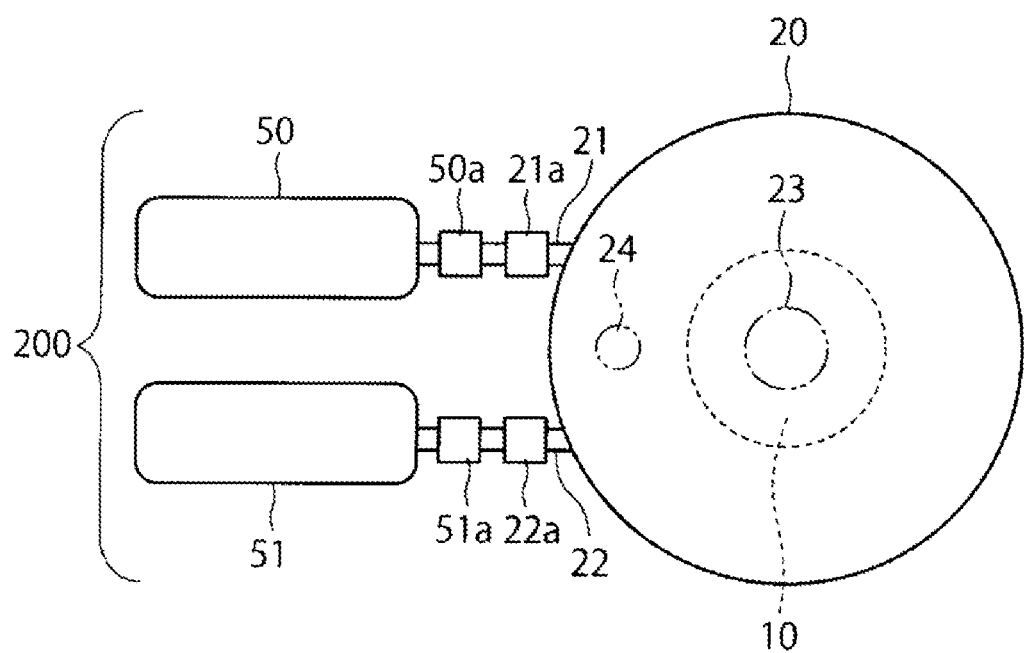
FIG. 17 is a diagram of a closed culture system 200 of the first embodiment.

A closed culture system 200 of the present embodiment includes, as illustrated in FIG. 17, the closed culture vessel 100 of the present invention, medium supply means 50 for supplying a culture medium to the closed culture vessel, and medium discharge means 51 for discharging the culture medium from the closed culture vessel.

The medium supply means 50 is connected to the culture solution inlet 21 of the closed culture vessel 100 of the present invention. The medium supply means 50 is capable of feeding a culture medium necessary for cell culture to the closed culture vessel 100 of the present invention. The medium supply means 50 may be provided with feed means (not illustrated) for feeding a culture medium. An example of the feed means includes a feed pump. The medium supply means 50 may also be placed in a position higher than the closed culture vessel 100 and the medium discharge means 51, so as to supply the culture medium to the closed culture vessel 100 by gravity. The medium supply means 50 preferably includes, in a passage connecting the airtight vessel 20 and the medium supply means 50, an adjustment mechanism 50a for adjusting a feeding rate of the culture solution. The adjustment mechanism 50a is, for example, a valve capable of adjusting a flow rate and stopping the flow.

The medium discharge means 51 is connected to the culture solution outlet 22 of the closed culture vessel 100 of the present invention. The medium discharge means 51 includes a stop mechanism 51a capable of stopping discharge of the culture solution. The stop mechanism 51a is, for example, a valve capable of stopping the flow.

(Operations of Closed Culture Vessel and Closed Culture System of First Embodiment)

Next, operations of the closed culture vessel 100 and the closed culture system 200 of the first embodiment will be described.

If the closed culture vessel of the present embodiment is a vessel that can be sealed after introducing the cell culture member 10 having cells adhered to the cell culture surface, cells are first seeded in the cell culture surface 10a of the cell culture member 10 so as to cause the cells to adhere to the cell culture surface 10a. Thereafter, the cell culture member 10 is introduced into the airtight vessel 10 which has been opened beforehand. After introducing the cell culture member 10, the airtight vessel 10 is sealed. The medium supply means 50 is aseptically connected to the culture solution inlet 21 of the sealed airtight vessel 10 and the medium discharge means 51 is aseptically connected to the culture solution outlet 22 of the airtight vessel, and thus, the closed culture system 200 can be obtained. Although not specifically limited as long as the cell culture surface 10a is covered with a culture medium, the airtight vessel 20 can be preferably completely filled with the culture medium or filled with the culture medium until the cell culture member 10 is completely hidden therein.

If the cell culture member 10 is precedently placed within the closed culture vessel 100 of the present embodiment, a cell suspension is first introduced into the airtight vessel 20, and thereafter, the medium supply means 50 is aseptically connected to the culture solution inlet 21 of the airtight vessel 10 and the medium discharge means 51 is aseptically connected to the culture solution outlet 22 of the airtight vessel, and thus, the closed culture system 200 can be obtained. Although not specifically limited as long as the cell culture surface 10a is covered with a culture medium, the airtight vessel 20 can be preferably completely filled with the culture medium or filled with the culture medium until the cell culture member 10 is completely hidden therein.

If the cell culture member 10 is precedently placed within the closed culture vessel 100 of the present embodiment, the cell culture member 10 is first taken out of the airtight vessel 20, and in the same manner as described above, cells may be caused to adhere to the cell culture surface 10a and the resultant may be aseptically introduced into the airtight vessel 20 before sealing the airtight vessel 20. The medium supply means 50 is aseptically connected through the connection means 50a to the culture solution inlet 21 of the airtight vessel 10 and the medium discharge means 51 is aseptically connected through the connection means 51a to the culture solution outlet 22 of the airtight vessel, and thus, the closed culture system 200 can be obtained.

The closed culture system 200 having cells adhered to the cell culture surface 10a can be introduced into a $CO_2$ incubator for cell culture to perform incubation. During the incubation, the medium supply means 50 can supply the culture medium to the airtight vessel 20 at a constant rate from the viewpoint of keeping constant the culture medium in the airtight vessel 20. The supply of the culture medium can be performed while discharging the culture medium by the medium discharge means 51.

After the cell culture, the on-off valves 21a and 22a are closed, and the closed culture vessel 100 is taken out of the closed culture system 200. The inside of the closed culture vessel 100 is kept in an aseptic state by the on-off valves 21a and 22a thus closed. Accordingly, the closed culture vessel 100 taken out of the closed culture system 200 can be carried from the cultivation room to another place (such as an operating room) with the internal aseptic environment retained. In the operating room, the airtight vessel of the closed culture vessel 100 is opened, and the cultured fresh cells (or cell sheet) can be taken out of the airtight vessel 20 together with the cell culture member 10. The cells can be easily peeled off from the cell culture member 10 taken out of the airtight vessel, and the cells can be easily transplanted to a patient.

In this manner, according to the present invention, the culture can be performed with the cell culture member 10 aseptically sealed in the airtight vessel 20, and after completing the culture, the cell culture member 10 can be carried in a state aseptically sealed in the airtight vessel 20. The present invention provides technical idea that the airtight vessel 20 is used not only as an outer wall of the closed culture vessel but also as means for protecting the cell culture member 10 from physical impact during transfer or from bacterial contamination, with an aseptic state of the cell culture member 10 kept. Furthermore, if the cell culture member 10 has a defect such as a minute pinhole, the defect can be easily detected based on leakage of a culture medium or change in the internal pressure. Since the airtight vessel 20 is openable, cells and the cell culture member can be easily taken out of the airtight vessel 20. Besides, since the cell culture member 10 can be taken out of the airtight vessel, the operations such as the peeling of cells from the cell culture member 10 and shape processing of a cell sheet on the cell culture member 10 can be easily performed. Furthermore, the closed culture vessel 100 of the present invention can be used for washing, differentiating or stimulating cells adhered to the cell culture member 10, and is advantageous in that such an operation can be aseptically practiced.

Second Embodiment

Figure 6:
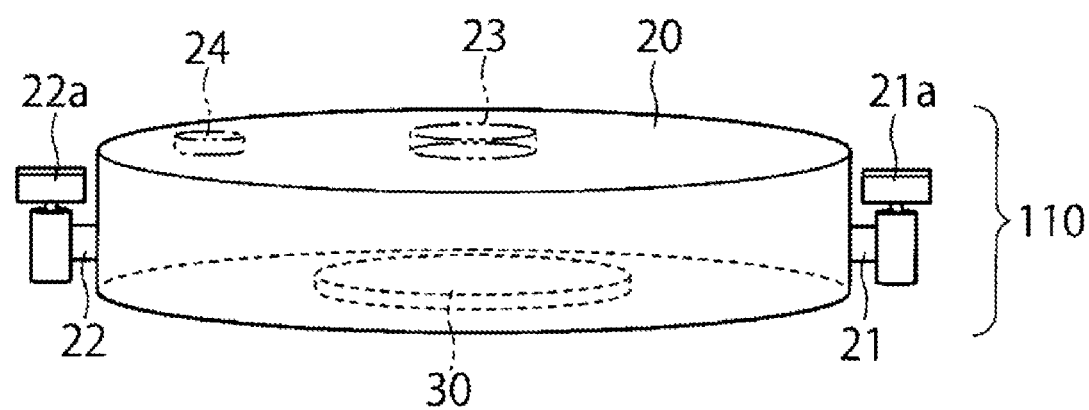
FIG. 6 is a diagram of a closed culture vessel 110 according to a second embodiment.
Figure 7:
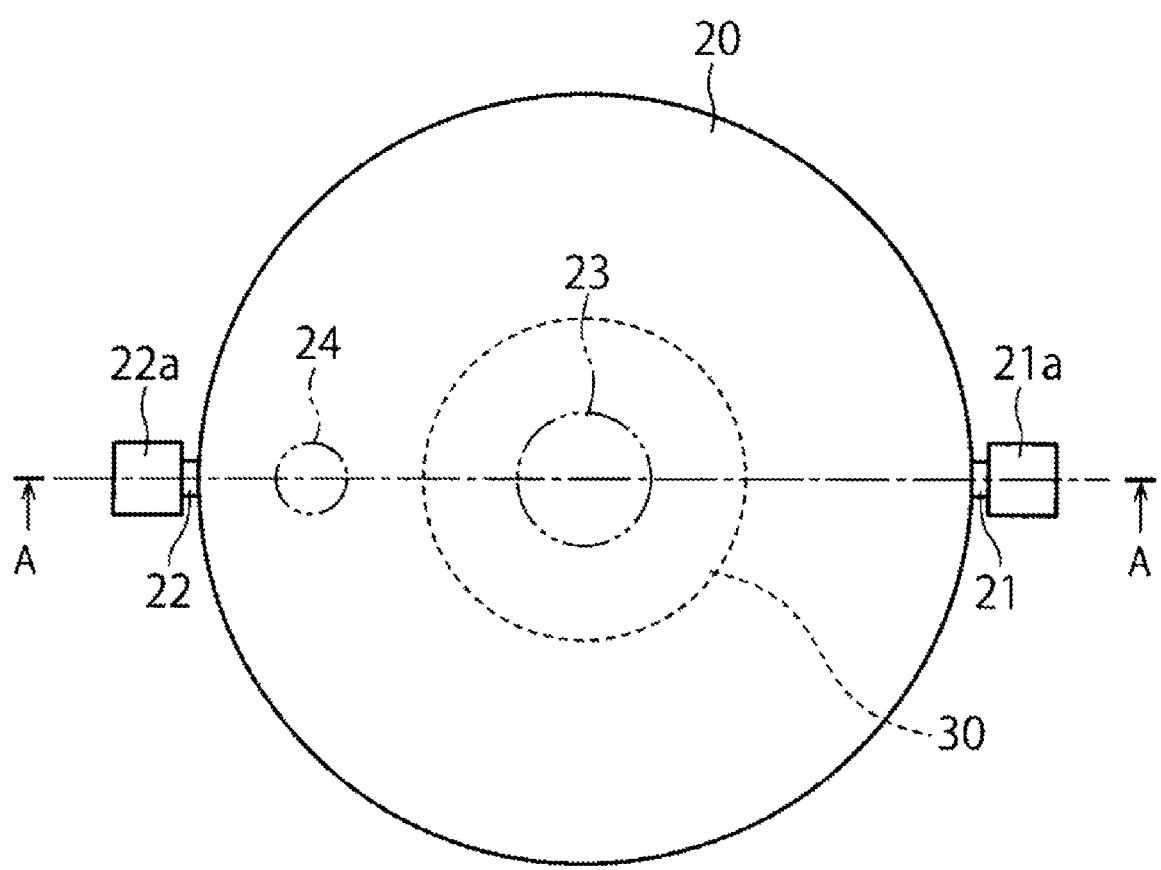
FIG. 7 is a plan view of the closed culture vessel 110 of the second embodiment.
Figure 8:
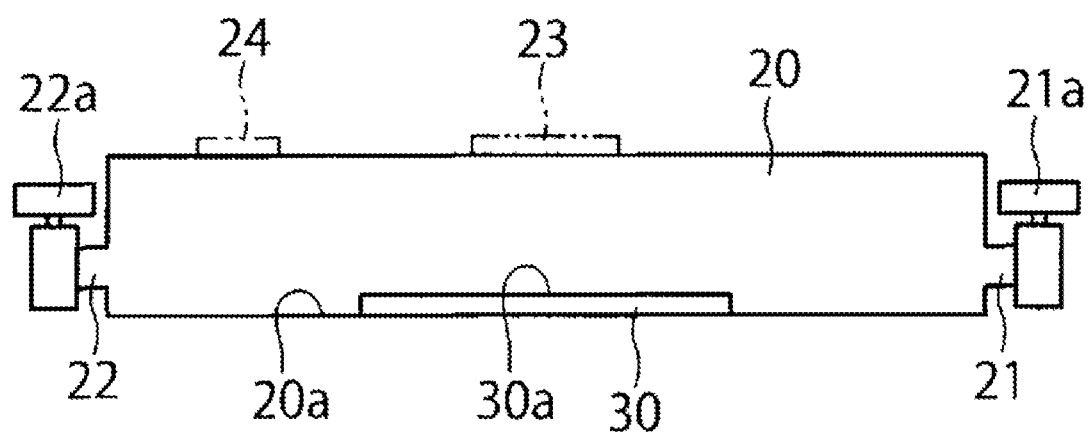
FIG. 8 is a cross-sectional view taken on line A-A of FIG. 7.

Next, a closed culture vessel 110 according to a second embodiment will be described with reference to FIGS. 6 to 8. The closed culture vessel of the second embodiment illustrated in FIGS. 6 to 8 has the same configuration as the closed culture vessel 100 of the first embodiment illustrated in FIGS. 1 to 3 except that the form of the cell culture member 10 is different. In FIGS. 6 to 8, like reference signs are used to refer to like elements of the closed culture vessel of the first embodiment illustrated in FIGS. 1 to 3 to omit the description.

Figure 9:
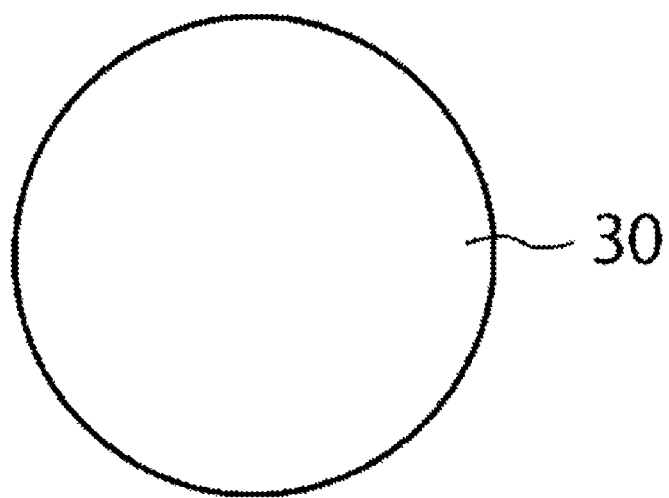
FIG. 9 is a plan view of a substrate 30.
Figure 10:
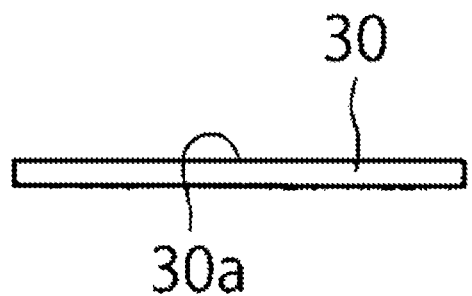
FIG. 10 is a cross-sectional view of the substrate 30.

As illustrated in FIGS. 9 and 10, the cell culture member 10 used in the closed culture vessel of the second embodiment is a substrate 30 having a cell culture surface 30a. The cell culture surface 30a of the substrate 30 is preferably subjected to the surface treatment for an adhesive surface to which adherent cells can adhere. The planar shape of the substrate 30 is not especially limited, and the substrate is in the shape of preferably a circle, an ellipse or a rectangle, for example, a square, a regular hexagon or a regular polygon.

In one aspect, the substrate 30 is a biological membrane. Examples of the biological membrane used as the substrate 30 include a collagen film and an amnion.

Figure 20:
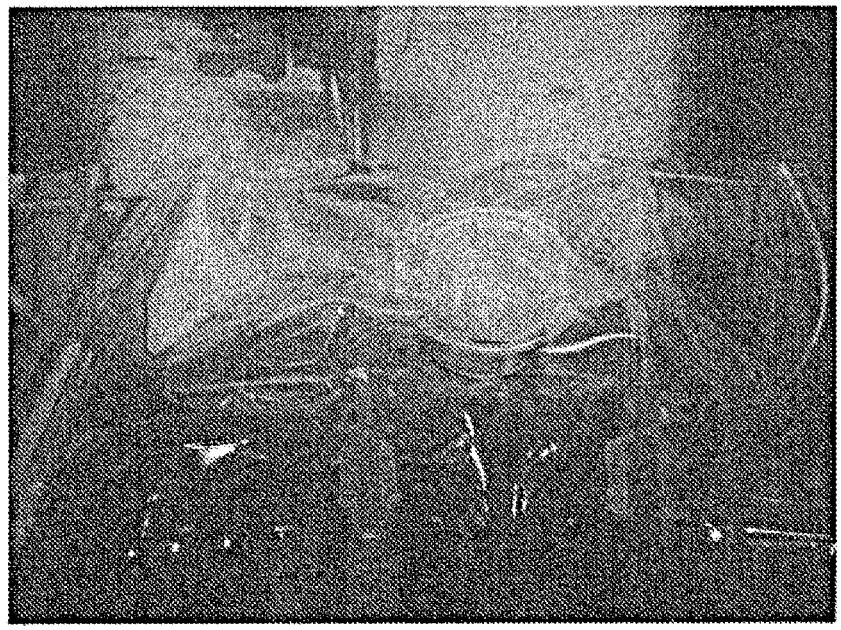
FIG. 20 is a photograph of a closed culture vessel produced in Example 1.

Advantages of using the substrate 30 as the cell culture member 10 are revealed in an example. Specifically, as in Example 2 and FIG. 20, cells seeded on the bottom surface 10a of the cell culture member spread to a side wall of the cell culture member during the culture. In various applications, cells adhered merely to the bottom surface 10a of the cell culture member are used, and hence, the substrate 30 is preferably used as the cell culture member from the viewpoint of reducing waste of cells and constantly controlling cell culture conditions. Besides, in this case, there is no need to separately control the cell adhesion on the bottom surface and the side wall, and hence, a merit that the processing cost of the cell culture member can be largely reduced can be obtained.

Figure 18:
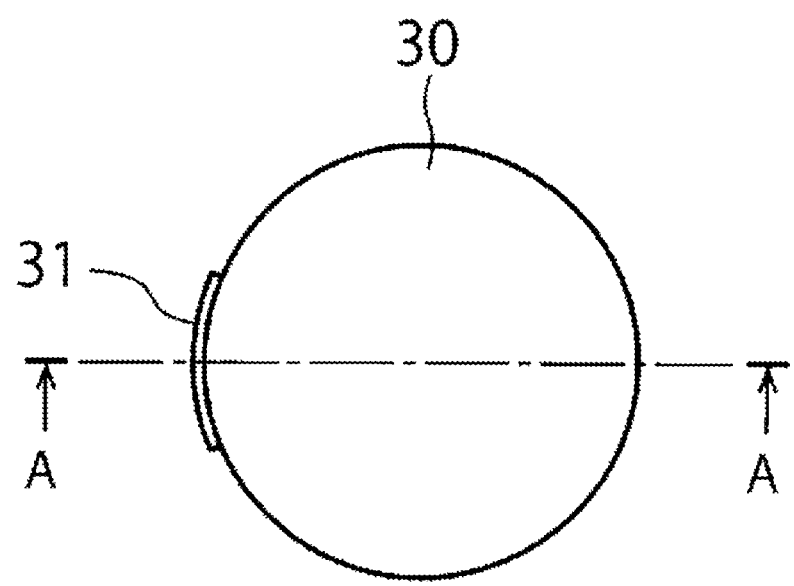
FIG. 18 is a diagram of the substrate 30 provided with a grip 31.
Figure 19:
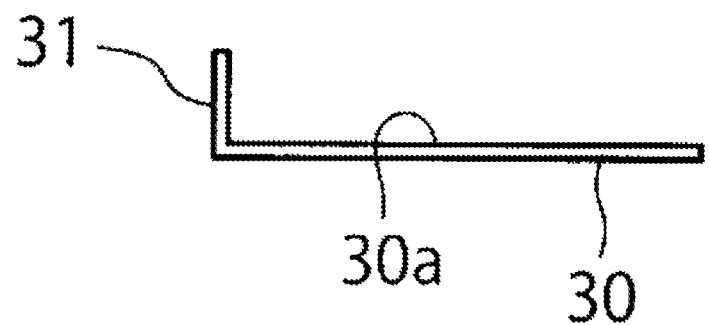
FIG. 19 is a cross-sectional view taken on line A-A of FIG. 18.

As illustrated in FIGS. 18 and 19, the cell culture member 10 is preferably provided with a grip 31 on its side surface. The cell culture member 10 can be easily taken out of the airtight vessel 20 by gripping the grip 31. The grip 31 can be, for example, a projection extending upward from a part of the circumferential edge of the substrate 30. The grip 31 is preferably subjected to neither the surface treatment for an adhesive surface nor the cell-adhesive coating, and is more preferably subjected to the non-cell-adhesive coating.

Third Embodiment

Next, a closed culture vessel 120 according to a third embodiment will be described with reference to FIGS. 11 to 13.

Figure 11:
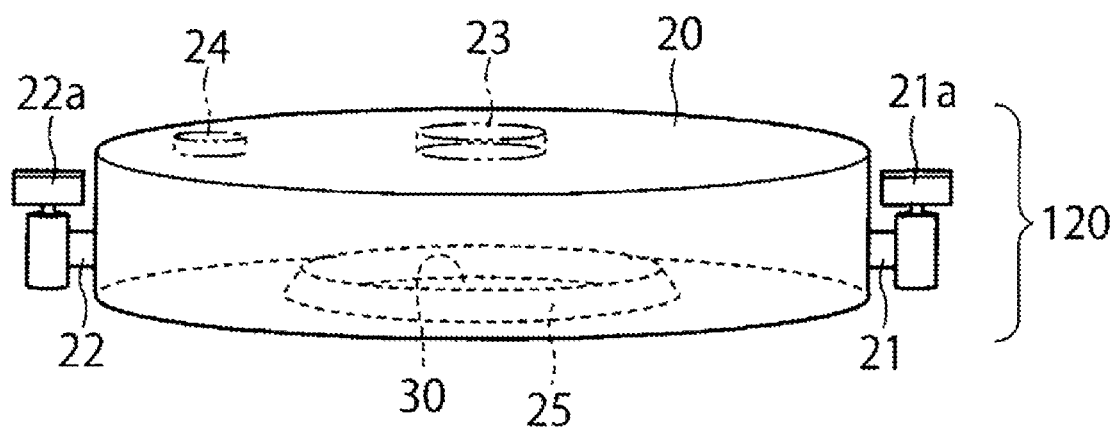
FIG. 11 is a diagram of a closed culture vessel 120 according to a third embodiment.
Figure 12:
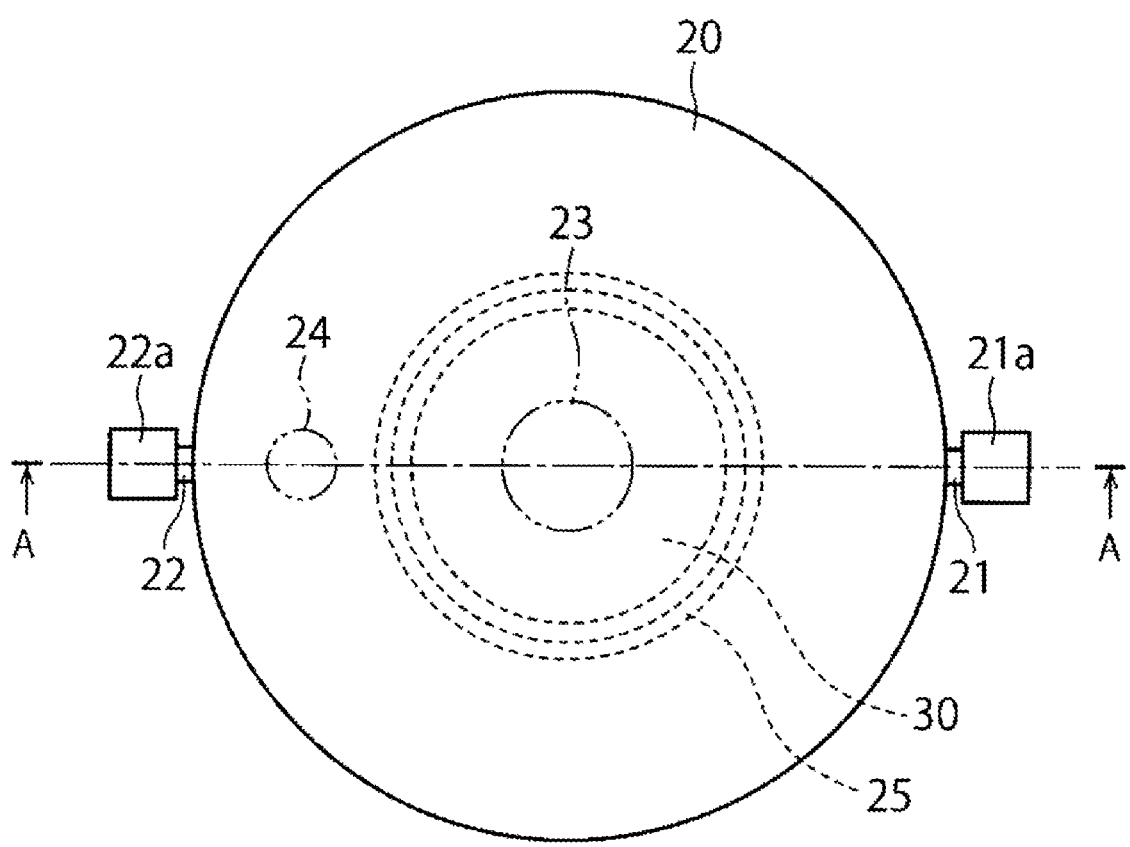
FIG. 12 is a plan view of the closed culture vessel 120 of the third embodiment.
Figure 13:
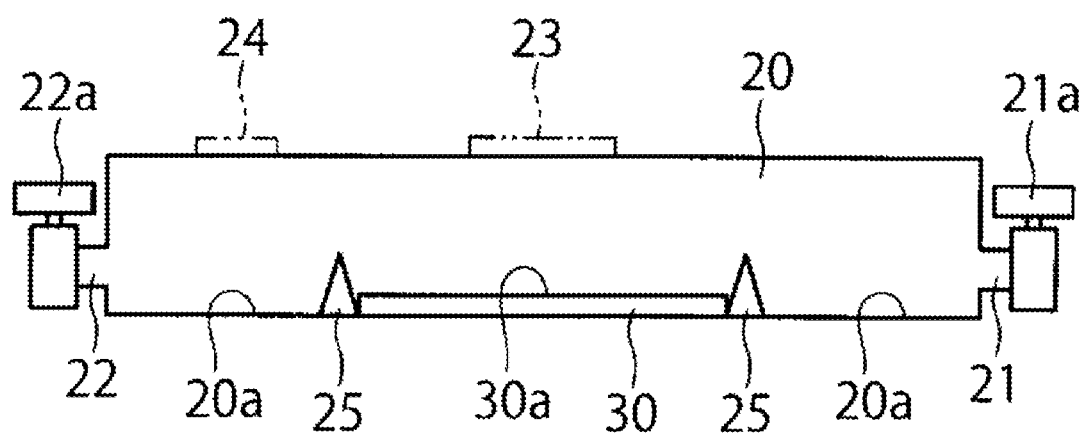
FIG. 13 is a cross-sectional view taken on line A-A of FIG. 12.

The closed culture vessel of the third embodiment illustrated in FIGS. 11 to 13 has the same configuration as the closed culture vessel 110 of the second embodiment illustrated in FIGS. 6 to 8 except that the form of the airtight vessel 20 is different. In FIGS. 11 to 13, like reference signs are used to refer to like elements of the closed culture vessel of the second embodiment illustrated in FIGS. 6 to 8 to omit the description.

In the closed culture vessel of the third embodiment illustrated in FIGS. 11 to 13, the airtight vessel 20 has a holding projection 25 for externally holding the substrate 30. The holding projection 25 can externally hold the substrate 30 to keep the substrate 30 in a prescribed position. There is a possibility that the concentration of a culture medium is uneven depending on positions in the closed culture vessel. Therefore, if the substrate 30 is held in a prescribed position, a culture environment of the substrate 30 in the closed culture vessel can be easily retained constant, which reduces variation in the physiological state and the growth state of cells among different substrates 30. Although the holding projection 25 is illustrated to be provided on the whole circumference of the substrate 30 in FIGS. 11 to 13 for convenience sake, the shape, the number and the arrangement thereof are not limited as long as the substrate 30 can be held in a prescribed position.

From the viewpoint of physically protecting the cell culture surface 30a of the substrate 30, the holding projection 25 preferably has a height larger than the thickness of the substrate 30. Thus, for example, the cell culture surface 30a can be protected from physical damage by the folding projection.

In one specific aspect, the substrate 30 has a grip 31. The grip 31 preferably has a height larger than the height of the holding projection 25. Thus, the substrate 30 can be easily collected from the airtight vessel 20. In one specific aspect, the holding projection 25 is broken in an arbitrary portion on the circumferential edge of the substrate 30. Thus, the substrate 30 can be easily collected by inserting tweezers through the broken portion (namely, a notch).

Modification of Third Embodiment

In a modification (not illustrated) of the third embodiment, a closed culture vessel has the same configuration as that of the third embodiment illustrated in FIGS. 11 to 13 except that the form of the cell culture member 10 is different.

In the modification of the third embodiment, the cell culture member 10 is the cell culture member 10 of the closed culture vessel of the first embodiment including the bottom surface 10a having the cell culture surface and the side surface 10b extending upward from the circumferential edge of the bottom surface. Owing to the side surface 10b extending upward from the circumferential edge of the bottom surface, the bottom surface 10a having the cell culture surface can be protected from physical damage.

Fourth Embodiment

A fourth embodiment relates to a set of the airtight vessel 20 and the cell culture member 10 for producing the closed culture vessel according to the first, second or third embodiment.

The set of the fourth embodiment is different, in that the airtight vessel 20 and the cell culture member 10 are separately provided and that the airtight vessel 20 is openable as well as sealable, from the first, second and third embodiments including the cell culture member 10 disposed inside the airtight vessel, but are the same as the first, second and third embodiments in other features.

In other words, in the fourth embodiment, the airtight vessel 20 can be any of the airtight vessels 20 described in the first, second and third embodiments as long as it is openable and sealable. From this point of view, the airtight vessel 20 of the fourth embodiment is preferably a cell culture bag.

Besides, in the fourth embodiment, the cell culture member 10 can be any of the cell culture members 10 described in the first, second and third embodiments. In a set of the fourth embodiment, the cell culture member 10 is preferably aseptically packaged by itself. Thus, the aseptic state of the cell culture member 10 can be kept, for example, when sold.

In the set of the fourth embodiment, the cell culture member 10 having cells seeded on the cell culture surface 10a is aseptically introduced into the airtight vessel 20, and then the airtight vessel 20 is sealed to form the closed culture vessel. The closed culture vessel thus formed using the set of the fourth embodiment is the same as any of the closed culture vessels of the first, second and third embodiments or the closed culture vessel of the modification of the third embodiment except that cells adhere to the cell adhesion surface 10a or 30a.

EXAMPLES

Example 1: Production of Closed Culture Vessel

In this example, a closed culture vessel of the present invention was produced by introducing a cell culture dish into a cell culture bag.

Corneal limbal cells including human corneal epithelial stem cells were seeded in Trans Well (product number: 3050) manufactured by Corning Inc., USA. As a culture medium, a DMEM/F12 medium containing B27 (manufactured by Life Technologies Corp., product number: 17504044) and 10 ng/mL keratinocyte growth factor (KGF, manufactured by Wako Pure Chemical Industries, Ltd., product number: 116-00811) was used. One day after the seeding, the culture bag manufactured by Nipro Corporation (product number: 87-352) was opened in an aseptic environment, the Trans Well was introduced into the culture bag, and the resultant bag was sealed with a sealer to obtain a closed culture vessel (see FIG. 20).

Example 2: Culture of Corneal Epithelial Cells Using Closed Culture Vessel

In this example, the corneal epithelial cells were cultured using the closed culture vessel.

Next, Terumo syringe 20 ml (SS-20ESZ) manufactured by Terumo Corporation equipped with a sterilizing filter Millex GP (SLGP033RB) manufactured by Millipore Corporation was used to introduce sterilized air into the closed culture vessel of the present invention, so as to inflate the bag to an extent not to press the Trans Well. Thereafter, means for supplying a culture medium was connected to the closed culture vessel of the present invention. Specifically, a medium inlet of the closed culture vessel obtained in Example 1 was aseptically connected to another culture bag manufactured by Nipro Corporation filled with a DMEM/F12 medium containing B27 and 10 ng/mL KGF.

Besides, means for discharging the culture medium was connected to the closed culture vessel of the present invention. Specifically, a medium outlet of the closed culture vessel was aseptically connected to an empty infusion set for children manufactured by Nipro Corporation (product number: TK-U750P).

Figure 21:
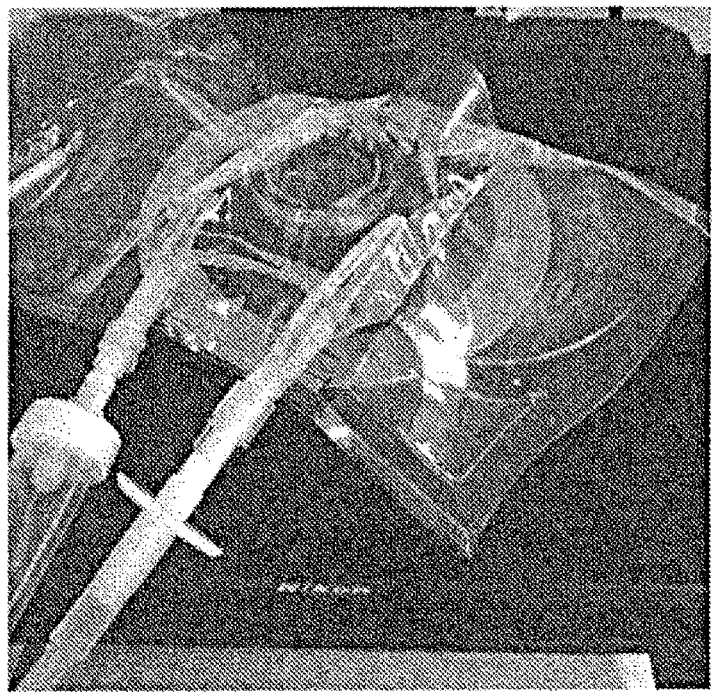
FIG. 21 is a photograph of a closed culture vessel taken while culturing cells in Example 2.

In this manner, a closed culture system was constructed (see FIG. 21).

Next, the culture medium was introduced into the closed culture vessel, and when the cells were sufficiently hidden in the culture medium, a clamp for adjusting a flow rate attached to a tube of the infusion set for children manufactured by Nipro Corporation was closed.

Thereafter, the thus obtained closed culture system was introduced into a $CO_2$ incubator for starting cell culture. Here, the means for supplying the culture medium was disposed on an upper shelf in the incubator, the closed culture vessel of the present invention was disposed on a middle shelf in the incubator, and the means for discharging the culture medium was disposed on a lower shelf in the incubator. The cells were cultured for 1 week without replacing the culture medium, and from day 8 when a cell colony had been sufficiently generated, the cells were cultured for 1 week with the culture medium replaced once two days. The replacement of the culture medium was performed by adjusting the clamp for adjusting the flow rate attached to the tube of the infusion set for children manufactured by Nipro Corporation so as to introduce a fresh culture medium by opening a passage and then closing the clamp. From day 15 after starting the culture when the cells were confirmed to be sufficiently grown, with the clamp for adjusting the flow rate attached to the tube of the infusion set for children manufactured by Nipro Corporation adjusted, a dropping rate of the discharged solution was measured for 3 minutes to adjust the flow rate of the culture medium to 1.75 mL/h. Thereafter, the cells were cultured for 1 week under general culture conditions, and thus, the culture was performed for 3 weeks in total.

Figure 22:
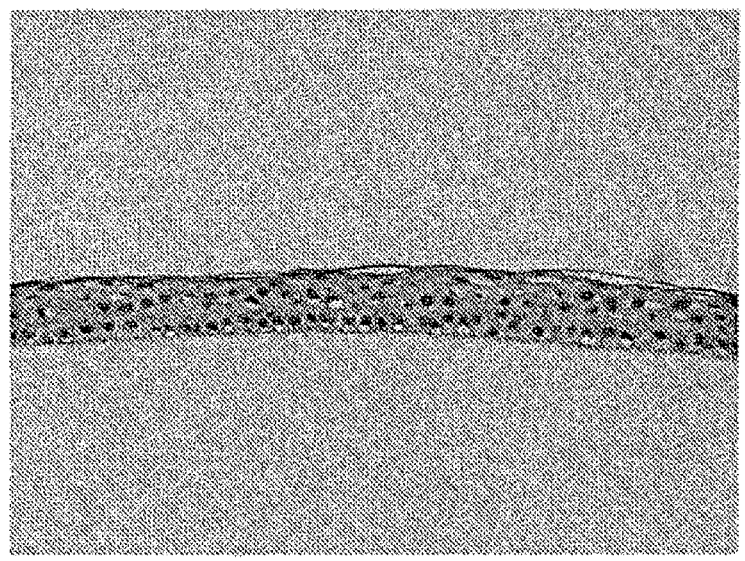
FIG. 22 illustrates corneal epithelial tissue obtained by culture in Example 2.

After completing the culture, the Trans Well was taken out of the bag, and a membrane having the cells adhered thereto was cut out from the Trans Well. The cut membrane was immobilized with 10% neutral buffered formalin (manufactured by Wako Pure Chemical Industries Ltd., product number: 062-01661), and a tissue preparation was stained with hematoxylin eosin by a usual method. A cross-section of the thus obtained tissue preparation was as illustrated in FIG. 22. It was revealed in FIG. 22 that the cultured corneal epithelial cells had a tissue structure similar to that of a corneal epithelial tissue having about 5 layers.

Figure 23:
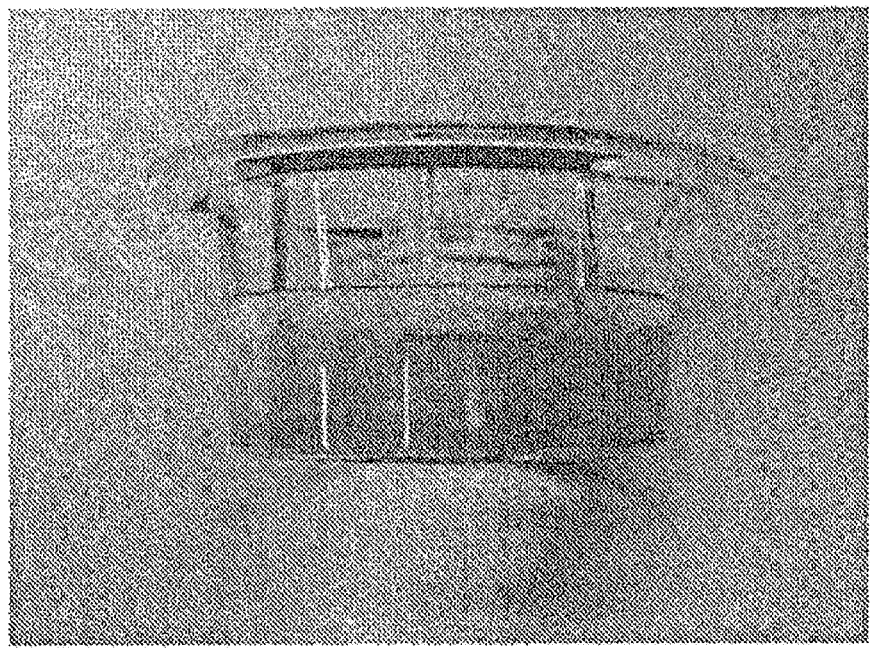
FIG. 23 illustrates a stained image of a cell adhesion surface of a cell culture member used in Example 2.

The Trans Well taken out of the bag was stained with an appropriate amount of rhodamine B (manufactured by Wako Pure Chemical Industries, Ltd., product number 180-00132) dissolved in water. Thus, the cells adhered to the side wall of the Trans Well were observed (FIG. 23).

The invention claimed is:

1. A closed cell culture system, comprising:
(i) a closed culture vessel for adherent cells comprising:
a gas permeable cell culture bag; and
an amnion membrane;
(ii) medium supply means for supplying a culture medium to the gas permeable cell culture bag; and
(iii) medium discharge means for discharging the culture medium from the gas permeable cell culture bag,
wherein the amnion membrane is provided inside the gas permeable cell culture bag;
wherein the amnion membrane is provided detachably from the gas permeable cell culture bag;
wherein the closed culture vessel comprises no culture medium;
wherein the supply means and the discharge means are aseptically closed; and
wherein the gas permeable cell culture bag has been aseptically sealed.

2. The closed cell culture system according to claim 1, wherein an inner surface of the gas permeable cell culture bag is non-cell-adhesive.

3. The closed cell culture system according to claim 1, wherein the gas permeable cell culture bag includes a cell inlet that is closed with a rubber plug through which adherent cells can be aseptically introduced onto a cell adhesion surface of the amnion membrane by using a syringe equipped with a needle that can penetrate through the rubber plug.

4. A method, comprising:
providing a closed culture vessel for adherent cells according to claim 1;
unsealing the gas permeable cell culture bag;
introducing an adhesive cell in a culture medium onto the amnion membrane inside the vessel to allow the adhesive cell to attach to the amnion membrane;
sealing the gas permeable cell culture bag to include a space therein formed by filling of the gas permeable cell culture bag with a culture medium and optionally a gas, thereby protecting a cell culture surface of the amnion membrane and cells adhered to the amnion membrane from physical damage; and then,
culturing the cell on the amnion membrane to form a cell sheet.

5. The method according to claim 4, further comprising aseptically transferring the closed culture vessel for adherent cells comprising the cell sheet to an operating room.

6. A method, comprising:
providing a closed culture vessel for adherent cells, comprising:
a gas permeable cell culture bag having a cell inlet; and
an amnion membrane,
wherein the amnion membrane is provided inside the gas permeable cell culture bag,
wherein the amnion membrane is provided detachably from the gas permeable cell culture bag;
wherein the closed culture vessel comprises no culture medium; and
wherein the cell inlet is aseptically closed with a rubber plug,
introducing an adhesive cell in a culture medium at least onto the amnion membrane inside the bag through the rubber plug by using a syringe equipped with a needle that can penetrate through the rubber plug to allow the adhesive cell to attach to the amnion membrane,
sealing the cell inlet of the gas permeable cell culture bag to include a space therein formed by filling of the gas permeable cell culture bag with a culture medium and optionally a gas, thereby protecting a cell culture surface of the amnion membrane and cells adhered to the amnion membrane from physical damage, and then,
culturing the cell on the amnion membrane to form a cell sheet.

7. The method according to claim 6, further comprising aseptically transferring the closed culture vessel for adherent cells comprising the cell sheet to an operating room.

* * * * *